United States Patent [19]

Pitzenberger et al.

[11] Patent Number: 4,780,538

[45] Date of Patent: Oct. 25, 1988

[54] PROCESS FOR 1,4-DIHYDROPYRIDINE COMPOUNDS USING A TITANAMINE CATALYST

[75] Inventors: Steven M. Pitzenberger, Lansdale, Pa.; Barry M. Trost, Madison, Wis.

[73] Assignee: Merck & Co., Inc., Rahway, N.J.

[21] Appl. No.: 828,474

[22] Filed: Feb. 12, 1986

[51] Int. Cl.$^4$ .................. C07D 211/02; C07D 211/90; C07D 401/04; C07D 413/04

[52] U.S. Cl. ................................ 546/249; 544/124; 544/216; 544/333; 544/364; 544/365; 544/405; 546/193; 546/194; 546/257; 546/271; 546/275; 546/276; 546/278; 546/279; 546/280; 546/281; 546/283; 546/284; 546/277; 546/321

[58] Field of Search .............................. 546/249, 321

[56] References Cited

U.S. PATENT DOCUMENTS

| | | | |
|---|---|---|---|
| 3,647,807 | 3/1972 | Bossert et al. | 546/321 |
| 4,258,042 | 3/1981 | Loev et al. | 544/131 |
| 4,472,411 | 9/1984 | Hatayama et al. | 546/321 |
| 4,551,467 | 11/1985 | Wehinger et al. | 546/321 |

OTHER PUBLICATIONS

Palecek, J. et al., Z. Chem., 14, 308–309 (1977).
Palecek, J. et al., Collection Czechoslouak Chem. Comm. 48, 608–16 (1983).
Iwanami, M. et al., Chem. Pharm. Bull., 27 1426–40 (1974).
Eisner, et al., Chem. Rev. 72, 1–53 (1972). Sausins, A. et al., Khim Geterolsike Soedin, 493–501 (1980).
Wilson, J. D. et al., J. Org. Chem., vol. 35, No. 5, (May 1970) pp. 1542–1545.

*Primary Examiner*—Mary C. Lee
*Assistant Examiner*—Dale A. Bjorkman
*Attorney, Agent, or Firm*—Alice O. Robertson; Michael C. Sudols, Jr.

[57] ABSTRACT

A process for the preparation of 1,4-dihydropyridine compounds, especially N-substituted 1,4-dihydropyridine compounds, is disclosed. The compounds are useful as cardiovascular agents and also as starting materials for the preparation of certain cyclized compounds which have properties as calcium entry blockers.

14 Claims, No Drawings

PROCESS FOR 1,4-DIHYDROPYRIDINE COMPOUNDS USING A TITANAMINE CATALYST

This invention is directed to a process for the preparation of 1,4-dihydropyridine compounds, particularly certain 2,6-dialkyl-3,5-dicarbalkoxy-N-substituted-1,4-dihydropyridines.

BACKGROUND OF THE INVENTION 1,4-Dihydropyridine compounds of the type represented by the formula:

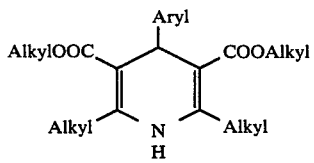

are known in the art. Many of the compounds are reported to have hypotensive and vasodilating properties, e.g. B. Loev, et al, J. Med. Chem., 17, 956–65 (1974). Also taught in the patent literature are compounds in which the nitrogen may be substituted with an alkyl or substituted alkyl group. These compounds are also taught to have activity useful in cardiovascular applications. However, the procedures reported for the preparation of such compounds have been limited in utility as a synthetic method, i.e., a method in which substantial quantities of the desired compound can reliably be prepared. The literature procedures for the preparation of N-alkyl-dihydropyridine compounds are generally of three types: (1) alkylation of dihydropyridine anions, e.g. J. Palecek and J. Kuthan, Z. Chem., 14, 308–9 (1974) and M. Iwanami, et al, Chem. Pharm. Bull., 27, 1426–40 (1979), (2) Hantzsch condensation with alkylamines, e.g. Bossert et al, U.S. Pat. No. 3,647,807, and (3) reduction of alkyl-pyridinium salts, e.g. U. Eisner and J. Kuthan, Chem. Rev., 72, 1–53 (1972). Each method has been found to have limitations as a synthetic procedure. The alkylation reaction is unsuitable, except for the simplest alkyl groups, giving low yields and product mixtures which are difficult to separate. The Hantzsch condensation procedure appears to work only with selected aniline compounds, e.g. A. Sausins, et al, Khim. Geterotsikl Soedin., 493–501 (1980). Thus, this method is not suitable for the preparation of N-alkyl or N-substituted alkyl-1,4-dihydropyridine compounds. Although a patent appears in the literature, U.S. Pat. No. 3,647,807, which purports to teach the preparation of N-alkyl compounds, the principal products have been found by modern spectrometric methods to be actually amino substituted cyclohexene or cyclohexadiene derivatives. The third method, the reduction of alkyl-pyridinium salts is a multi-step procedure, generally resulting in very poor yields. Thus, an efficient method is desired for the preparation of known cardiovascular agents. In addition, an efficient method for the preparation of N-substituted alkyl-1,4-dihydropyridine compounds was desired in connection with studies for the intramolecular additions to the dihydropyridine ring system.

DESCRIPTION OF THE INVENTION

The present invention is directed to a process for the preparation of a dihydropyridine compound represented by the formula:

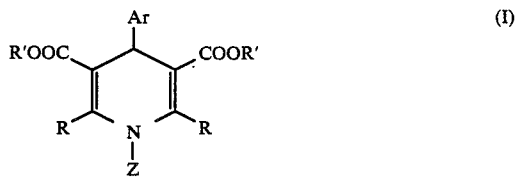

in good yields and in good purity, by reacting an aminoalkenoate ester represented by the formula:

and an aryl aldehyde compound represented by the formula:

in the presence of a titanamine reagent, wherein Ar may be a substituted or unsubstituted carbocyclic aryl or heterocyclic aryl radical, R may be alkyl or substituted alkyl, R' may be alkyl, alkenyl, cycloalkyl, benzyl or substituted alkyl, and Z may be hydrogen, alkyl, alkenyl, alkynyl, cycloalkyl, tolyl, phenyl, substituted alkyl, substituted alkenyl or substituted alkynyl as hereinafter more fully defined.

By "titanamine reagent" or "titanamine complex" as herein employed is meant a complex of titanium tetrachloride and an amine base, formed when titanium tetrachloride is contacted with an amine base as subsequently discussed.

By use of the titanamine reagent it has been possible to obtain in good yields certain dihydropyridine compounds which were heretofore difficult to obtain or to obtain more facilely certain other dihydropyridine compounds than could be obtained by the Hantzsch condensation reaction. Thus, when dihydropyridine compounds which are represented by Z as alkyl in Formula I are attempted to be prepared by the Hantzsch reaction, usually an aminocyclohexene and/or an aminocyclohexadiene compound are produced as major product or products. By use of the titanamine reagent, it has been found not only that the dihydropyridine compound is obtained as the major product but also that the rate of reaction is increased, thereby facilitating the formation of the desired dihydropyridine product. When Z is aryl or hydrogen, it has been possible to produce dihydropyridine compounds in good yields in a conventional Hantzsch condensation. However, the use of titanamine reagent nevertheless has been found to be unexpectedly advantageous in increasing the reaction rate and in lowering the reaction temperature.

The process of the present invention is adaptable to the preparation of a wide range of compounds, limited only by the desirable absence of functional groups such as hydroxyl, thiol, carboxylic acid, enolizable ketone, primary amino and the like which are capable of side reactions in the presence of titanamine reagent. While it may be necessary to consider certain groups which would ultimately occupy the 2 and 6 positions of the dihydropyridine ring from the standpoint of steric considerations, the process is not otherwise limiting.

The compounds which may be prepared by the process of the present invention are represented by Formula I in which Ar is a carbocyclic aryl radical, a heterocyclic aryl radical, a substituted carbocyclic aryl radical with up to three substituents, a substituted heterocyclic aryl radical with up to two substituents, perfluorophenyl or benzoxadiazolyl; wherein the carbocyclic aryl radical is of 6 or 10 atoms, the heterocyclic radical is of 5 or 6 atoms of which one or two is a heteroatom selected from O, S or N, and in the substituted radicals, the substituent is selected from $C_1$-$C_8$ alkyl, $C_2$-$C_8$ alkenyl, $C_1$-$C_8$ alkoxy, $C_2$-$C_8$ alkoxyalkyl, $C_1$-$C_2$ alkylenedioxy, $C_2$-$C_8$ dialkylamino, $C_1$-$C_8$ alkylthio, chloro, fluoro, bromo, iodo, cyano, nitro, trifluoromethyl, and mono- and polyhalomethoxy wherein the halo may be fluoro, chloro or bromo;

R is alkyl or substituted alkyl; wherein when alkyl, it is of 1 to 8 carbon atoms and when substituted alkyl, the alkyl portion is of 1 to 3 carbon atoms and the substituent is selected from $C_1$-$C_4$ alkoxy and $C_1$-$C_4$ mono- or polyhaloalkyloxy wherein the halo may be fluoro, chloro or bromo;

R' is alkyl, alkenyl, cycloalkyl, substituted alkyl or benzyl; wherein alkyl is of 1 to 8 carbon atoms, alkenyl is of 2 to 8 carbon atoms, cycloalkyl is of 3 to 6 carbon atoms, and substituted alkyl is of 2 to 4 carbon atoms in the alkyl portion and is substituted at the 2 or higher position with a substituent selected from $C_1$-$C_8$ alkoxy, fluoro, chloro, bromo, $C_2$-$C_8$ dialkylamino, phenyl, and a heterocyclic aryl radical of 5 or 6 atoms containing up to 3 hetero atoms selected from O, S and N;

Z is hydrogen, alkyl, alkenyl, alkynyl, phenyl, tolyl, cycloalkyl, phenyl substituted alkyl, substituted alkenyl and substituted alkynyl; wherein alkyl is a radical of from 1 to 10 carbon atoms; alkenyl is a radical of from 3 to 10 carbon atoms with the olefinic unsaturation occurring at the 2 or higher position; alkynyl is a radical of from 3 to 10 carbon atoms with the acetylenic unsaturation occurring at the 2 or higher position; cycloalkyl is a radical of from 3 to 6 carbon atoms; substituted alkyl is a radical of up to 10 carbon atoms in the alkyl portion and wherein the substituent may be selected from Ar as above-defined, $C_3$-$C_6$ cycloalkyl or $C_2$-$C_8$ carboalkoxy, or when the alkyl group is at least of 2 carbon atoms, it may be substituted at the 2 or higher position with a substituent selected from $C_1$-$C_8$ alkoxy, $C_1$-$C_8$ alkylthio, fluoro, chloro, bromo, $C_2$-$C_8$ dialkylamino, phenoxy, phenylthio, morpholino, piperidino, pyrrolidino, piperazino and $C_2$-$C_8$ acyloxy; substituted alkenyl wherein the substituent is selected from Ar as above defined, $C_3$-$C_6$ alkyl, and $C_2$-$C_8$ carboalkoxy; and substituted alkynyl wherein the substituent is selected from Ar as above defined, $C_3$-$C_6$ cycloalkyl and $C_2$-$C_8$ carboalkoxy.

Representative radicals within carbocyclic aryl radical of 6 or 10 atoms are phenyl and the naphthyl radicals. Representative radicals within the expression "heterocyclic radical of 5 or 6 atoms containing up to two heteroatoms selected from O, S or N", include furyl, pyrrolyl, pyridyl, thienyl, oxazolyl, thiazolyl, isoxazolyl, isothiazolyl, pyrimidinyl, pyrazinyl, pyrazolyl, isopyrazolyl, imidazolyl and isoimidazolyl. Representative radicals when the expression "heterocyclic radical of 5 or 6 atoms containing up to three hetero atoms selected from O, S or N," include, in addition to the above-named radicals, triazolyl, triazinyl, oxadiazolyl, oxathiazolyl and thiadiazolyl.

When the substituent is a halogen and it is of multiple occurrence mixed halogen substitutions are intended to be included.

The present invention is particularly directed to a process for the preparation of N-substituted dihydropyridine compounds represented by the formula

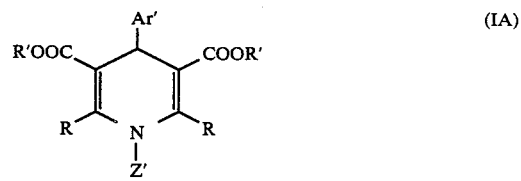

(IA)

especially where Z' is a group in which a carbon is attached to the nitrogen and the carbon is saturated carbon as hereinafter detailed. Compounds in which Z' is a group in which the carbon to be attached to the nitrogen is a saturated carbon are difficult to prepare by conventional methods suitable for the preparation of dihydropyridine compounds. Particularly difficult are those compounds in which Z' is a substituted ethyl group, as seen in J. Palecek, et al. Collect. Czeck. Chem. Commun., 48, 608-16 (1983). Thus, the process of this invention is especially useful for the preparation of such compounds although it is also useful for the preparation of compounds in which Z is hydrogen or an aromatic group.

In the compounds represented by Formula IA,

Ar' is phenyl; substituted phenyl with up to 3 substituents selected from $C_1$-$C_8$ alkyl, $C_2$-$C_8$ alkenyl, $C_1$-$C_8$ alkoxy, $C_2$-$C_8$ alkoxyalkyl, $C_1$-$C_2$ alkylenedioxy, $C_2$-$C_8$ dialkylamino, $C_1$-$C_8$ alkylthio, fluoro, chloro, bromo, iodo, trifluoromethyl, cyano, nitro, and mono- and polyhalomethoxy wherein the halo may be fluoro, chloro, or bromo; perfluorophenyl; or benzoxadiazolyl;

R is $C_1$-$C_8$ alkyl, or $C_1$-$C_3$ substituted alkyl with the substituent selected from $C_1$-$C_4$ alkoxy and $C_1$-$C_4$ mono- or polyhalo alkoxy wherein the halo is selected from fluoro, chloro and bromo;

R' is $C_1$-$C_8$ alkyl; $C_2$-$C_8$ alkenyl; $C_3$-$C_6$ cycloalkyl; $C_2$-$C_4$ substituted alkyl wherein the substituent is at a 2 or higher position and is selected from $C_1$-$C_8$ alkoxy, halo wherein said halo is fluoro, chloro or bromo, $C_2$-$C_8$ dialkylamino, phenyl, and a heterocyclic aryl radical of 5 or 6 atoms containing up to 3 hetero atoms selected from O, S and N; or benzyl;

Z' is $C_1$-$C_{10}$ alkyl; $C_3$-$C_{10}$ alkenyl wherein the acetylenic unsaturation occurs at the 2 or higher position; $C_3$-$C_{10}$ alkynyl wherein the olefinic unsaturation occurs at the 2 or higher position; $C_3$-$C_6$ cycloalkyl; $C_1$-$C_{10}$ substituted alkyl with the substituent selected from Ar' as above defined, $C_3$-$C_6$ cycloalkyl, $C_2$-$C_8$ carboalkoxy, naphthyl, and a heterocyclic radical of 5 or 6 carbon atoms of which one or two is a hetero atom selected from O, S, and N, and which heterocyclic radical may be substituted with $C_1$-$C_4$ alkyl; $C_2$-$C_{10}$ substituted alkyl with the substituent at the 2 or higher position and the substituent is selected from $C_1$-$C_8$ alkoxy, $C_1$-$C_8$ alkylthio, fluoro, chloro, bromo, iodo, C$_2$–C$_8$ dialkylamino, phenoxy, phenylthio, morpholino, piperidino, pyrrolidino, piperazino and C$_2$–C$_8$ acyloxy; C$_3$–C$_{10}$ alkenyl substituted with a substituent selected from Ar' as above defined, C$_3$–C$_6$ cycloalkyl, and C$_2$–C$_8$ carboalkoxy; C$_3$–C$_{10}$ alkynyl substituted with a substituent selected from Ar' as above defined, C$_3$–C$_6$ cycloalkyl, and C$_2$–C$_8$ carboalkoxy.

The compounds for which the process of the present invention would find most frequent application are those compounds which may be represented by Formula IB.

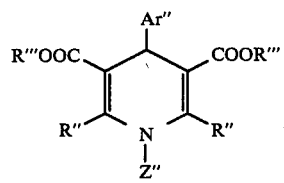

wherein

Ar'' is perfluorophenyl; benzoxadiazolyl; or a radical represented by

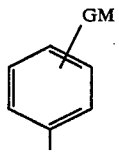

wherein G is C$_1$–C$_8$ alkyl; C$_2$–C$_8$ alkenyl; C$_1$–C$_8$ alkoxy, C$_2$–C$_8$ alkoxyalkyl, C$_1$–C$_2$ alkylenedioxy, C$_2$–C$_8$ dialkylamino, C$_1$–C$_8$ alkylthio, fluoro, chloro, bromo, iodo, trifluoromethyl, cyano, nitro, and mono- and polyhalomethoxy wherein halo is selected from fluoro, chloro and bromo; and m is 0–3;

R'' is C$_1$–C$_8$ alkyl, or C$_2$–C$_8$ alkoxyalkyl;

R''' is C$_1$–C$_8$ alkyl; C$_2$–C$_8$ alkenyl; C$_2$–C$_4$ substituted alkyl wherein the substituent is at the 2 or higher position and is selected from C$_1$–C$_8$ alkoxy, C$_2$–C$_8$ dialkylamino, phenyl and pyridyl; or benzyl; and Z'' is C$_1$–C$_{10}$ alkyl; C$_3$–C$_{10}$ alkenyl wherein the olefinic unsaturation occurs at the 2 or higher position; C$_3$–C$_{10}$ alkynyl wherein the acetylenic unsaturation occurs at the 2 or higher position; C$_3$–C$_6$ cycloalkyl; C$_1$–C$_{10}$ substituted alkyl with the substituent selected from Ar'' as above defined, C$_3$–C$_6$ cycloalkyl, C$_2$–C$_8$ carboalkoxy, naphthyl, and a heterocyclic radical of 5 or 6 carbon atoms of which one or two is a hetero atom selected from O, S, and N, and which heterocyclic radical may be substituted with C$_1$–C$_4$ alkyl; C$_2$–C$_{10}$ substituted alkyl with the subtituent at the 2 or higher position and the substituent selected from C$_1$–C$_8$ alkoxy, C$_1$–C$_8$ alkylthio, fluoro, chloro, bromo, iodo, C$_2$–C$_8$ dialkylamino, N-alkylanilino, phenoxy, phenylthio, morpholino, piperidino, pyrrolidino, piperazino and C$_2$–C$_8$ acyloxy; C$_3$–C$_{10}$ alkenyl substituted with Ar'' as above defined, C$_3$–C$_6$ cycloalkyl, or C$_2$–C$_8$ carboalkoxy; C$_3$–C$_{10}$ alkynyl substituted with Ar'' as above defined, C$_3$–C$_6$ cycloalkyl, and C$_2$–C$_8$ carboalkoxy.

Representative specific groups for the Z substituents include methyl, t-butyl, n-hexyl, allyl, propargyl, 3-butenyl, cyclohexyl, crotyl, isopentyl, isopropyl, 2-dimethylaminoethyl, 3-ethoxypropyl, 2-piperidinoethyl, 2-carboethoxyethyl, 1-carboethoxypropyl, 2-phenylethyl, 2-(2-pyridyl)ethyl, 2-(2-thienyl)ethyl, 2-(1-naphthyl)ethyl, 2-(2-furanyl)propyl, 2-cyclohexylethyl, 2-piperidinoethyl, 2-(4-methylphenyl)propyl, (2-(4-chlorophenyl)ethyl, benzyl, 2-phenylpropyl, 2-(2-methylphenyl)ethyl, 2-(3,4-dimethoxyphenyl)butyl, 2-(3-thienyl)ethyl, 3-(3-methyl-5-isoxazolyl)propyl, 2(2-thiazolyl)ethyl, 2-(3-benzothienyl)ethyl, 2-(5-benzofuranyl)ethyl, 2-(3,4-dimethoxyphenyl)ethyl, 2-(3-pyridyl)propyl and the like.

Representative of substituted phenyl groups as Ar which may be present in the compounds prepared by the process of the present invention include 2-nitrophenyl, 2,4,6-trichlorophenyl, 2,4,5-trimethylphenyl, 2-trifluoromethylphenyl, 3-methoxyphenyl, 3-iodophenyl, 2-methylphenyl, 3-trifluoromethylphenyl, 2-chlorophenyl, 4-carboethoxyphenyl, 3-ethoxyphenyl, 2-cyanophenyl, 2,3-dichlorophenyl, 5-chloro-2-nitrophenyl, 2-chloro-4-nitrophenyl, 4-ethoxymethylphenyl, 4-methoxymethylphenyl, 3-propoxyphenyl, 4-(isopropoxyethyl)phenyl and 4-cyanophenyl. Still others include 4-crotylphenyl, 3,4-methylenedioxyphenyl, 3,4-dibromophenyl, 4-(n-propoxy)ethylphenyl, 4-diethylaminophenyl, 2-methylthiophenyl and the like.

A preferred embodiment of the process of the present invention comprises preparing a titanamine reagent in an inert solvent and adding dropwise to the titanamine dispersion under an inert atmosphere of argon or nitrogen, an appropriate alkyl 3-amino-2-alkenoate (hereinafter "aminoalkenoate compound") and an appropriate aromatic aldehyde.

The exact nature of the titanamine reagent or the titanium tetrachloride-amine base complex has not yet been determined but it has been determined that there is an initial reaction between the titanium tetrachloride and the amine base to form a species responsible for the catalytic effect. The amines which may be employed to form the titanamine reagent can be considered to fall into two categories: (1) those which form a complex with the titanium tetrachloride and do not become part of the final product and (2) those which form a complex with the titanium tetrachloride and which are incorporated at least in part in the final dihydropyridine structure.

Amines which may be employed to form a titanamine reagent but which do not become part of the dihydropyridine compound are found to be of two different classes (a) secondary amines and (b) tertiary trimethylsilylamines. Representative secondary amines include piperidine, morpholine, dimethylamine, diethylamine, di-n-propylamine, pyrrolidine, N-methylaniline and imidazole but are not limited thereto. Representative tertiary trimethylsilylamines include N-(trimethylsilyl)piperidine, 4-(trimethylsilyl)morpholine, N,N-di(methyl)trimethylsilylamine, N,N-di(ethyl)trimethylsilylamine and N-(trimethylsilyl)pyrrolidine but are not limited thereto.

Amines which may be employed to form a titanamine reagent and which do become part of the dihydropyridine structure are primary amines identical to those used to prepare the aminoalkenoate compounds.

Generally, the substituted aminoalkenoate compound is prepared prior to the carrying out of the reaction inasmuch as it is not generally a readily available starting material. The substituted aminoalkenoate compound is prepared from an acylacetic ester and appropriate amine:

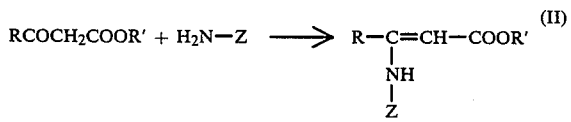

or

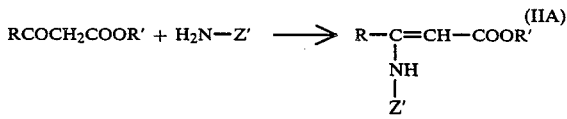

or

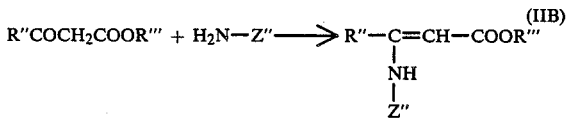

In carrying out this step, one reactant is added dropwise to the stirred solution of the other reactant and the stirring continued for time sufficient to obtain an alkyl 3-(substituted)amino-2-alkenoate compound (II, IIA or IIB).

About equimolar amounts of the alkyl acylacetate and amine compound are employed. The reaction is carried out by the dropwise addition of one reactant to the other. The temperature of reaction may vary from about 0° C. to ambient temperature. When the reactant amine is one in which the Z group has aliphatic unsaturation, cooling is preferred. When the reactant amine is an arylalkylamine, the reaction may be carried out at ambient temperature. The reactants are intimately contacted such as by stirring from about 1 hour to 12 hours. As a result of these operations, the desired substituted aminoalkenoate intermediate is formed in the reaction mixture. It may be recovered therefrom by diluting the reaction mixture with water-immiscible organic solvent, washing the organic selution with brine, drying the organic solution over drying agent and then evaporating the solvent to obtain the intermediate as residue. Water-immiscible solvents such as ethereal, hydrocarbon and halohydrocarbon solvents and the like are suitable in this recovery step.

The titanamine reagent is next prepared. It is prepared by adding an organic amine dropwise under an inert atmosphere to a stirred solution of titanium tetrachloride in an inert solvent such as benzene. The titanamine reagent forms therein and the resulting mixture is employed without modification.

The relative amounts of amine and titanium tetrachloride employed to form a complex depends on the type of amine base employed to form the complex. When the amine base is the same as that in the substituted aminoalkenoate compound which enters into the structure of the final product, a ratio of amine base to titanium tetrachloride of about 2.5:1 to 1.8:1, generally 2:1 is employed. When the amine base of an amine which is not incorporated into the final structure, the preferred ratio of amine base to titanium tetrachloride depends on the base. When the base is a secondary amine base, approximately 2:1 ratio (range of 2.5:1 to 1.8:1) of amine base to titanum tetrachloride is employed. When the amine base is a tertiary trimethylsilylated amine, then an approximately 1:1 ratio (range of 1.2:1 to 0.8:1) is preferred.

The titanamine reagent is prepared in an inert solvent such as benzene, toluene, chloroform, methylene chloride, and the like. Non-polar solvents such as benzene are preferred for the condensation reaction in which the reagent is employed.

The substituted aminoalkenoate prepared as above described is then reacted with a substantially half-molar amount of aryl aldehyde in the presence of an about half molar equivalent (based on aldehyde) of titanium reagent, prepared as above described, in accordance with the following equations:

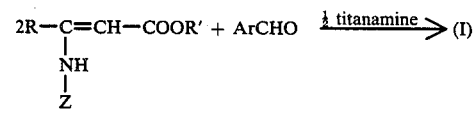

or

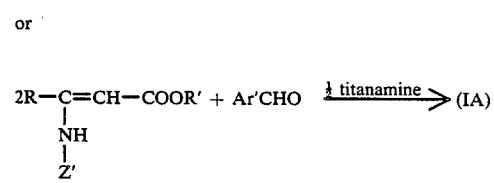

or

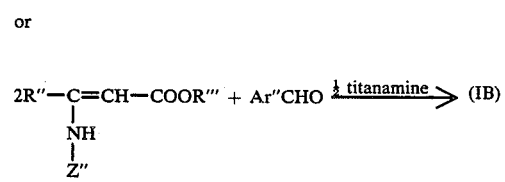

The foregoing reaction is carried out in the medium in which the titanamine reagent has been prepared. In carrying out the reaction, the aminoalkenoate compound and the appropriate aryl aldehyde compound dissolved in a suitable inert organic solvent are added to the titanamine solution. The aminoalkenoate and aryl aldehyde may be mixed in the solution or may be added sequentially. The resulting mixture is stirred for from about 1 to 20 hours to obtain the desired dihydropyridine compound in the reaction mixture. At the end of the reaction period, the reaction is quenched by adding dilute acid. The dihydropyridine ccompound is recovered from the mixture by extracting with a water-immiscible organic solvent and thereafter washing and drying the organic solution in a conventional manner and recovering the product as residue. The product may be purified by flash chromatography (J. Org. Chem. 43, 2923 (1978)) or by other suitable means. The product then may be crystallized or recrystallized in a conventional manner.

The process of the present invention has been especially useful for the preparation of compounds represented by the formula:

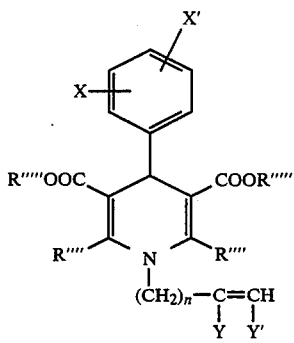

(IC)

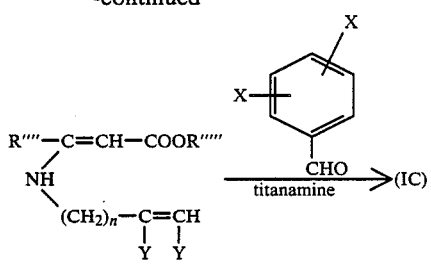

which are intermediates for the preparation of compounds represented by the following formulas:

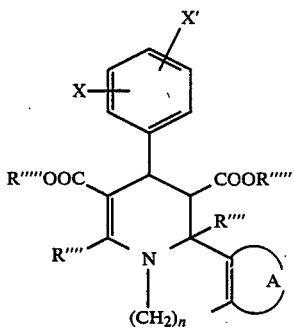

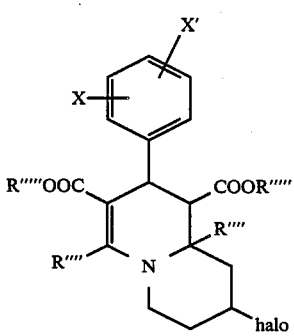

In the formulas, X and X' are independently hydrogen, halogen, lower alkyl, lower alkoxy, nitro or trifluoromethyl; R'''' and R''''' are lower alkyl, and A is —CH=CH—S—, —CH=CH—O—, —CH=CH—NH— or —CH=CH—NAlk wherein Alk is lower alkyl, Y and Y' are H or lower alkyl or together are A, n is 2 or 3. These compounds are prepared using the process of the present invention in accordance with the equation

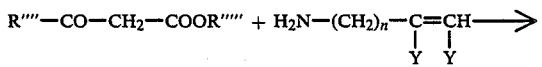

These compounds, useful as calcium entry blockers are disclosed and claimed in copending applications Ser. No. 802,127, filed Nov. 26, 1987, abandoned of George Hartman et al., and Ser. No. 802,128, filed Nov. 26, 1987, now U.S. Pat. No. 4,721,708 of George Hartman et al.

The following examples illustrate the invention but are not to be construed as limiting.

EXAMPLE I

Dimethyl 1-Benzyl-2,6-dimethyl-4-(2-methylphenyl)-1,4-dihydropyridine-3,5-dicarboxylate

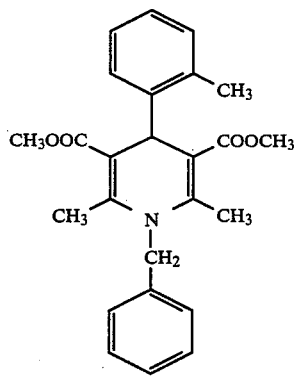

Preparation of methyl 3-benzylaminocrotonate 96.4 grams (0.9 mole) of benzylamine was added dropwise with stirring while the temperature was maintained below 45° C. to a solution of 116.1 grams (1 mole) of methyl acetoacetate and the reaction mixture allowed to stand overnight to obtain a white solid. The latter was dried and then stripped of the solvent to obtain a residue which was crystallized from hexane to obtain 115.9 grams of the methyl 3-benzylaminocrotonate, m.p. 36°-37.5° C. 4.1 grams (20 millimoles) of the product was dissolved in 5 milliliters of benzene and used in the preparation of the dihydropyridine compound.

Preparation of titanamine complex 0.55 milliliter (5 millimoles) of titanium tetrachloride was added to 20 milliliters of dry benzene under an atmosphere of argon. To the solution was added with stirring 0.80 milliliter (5 millimoles) of 4-(trimethylsilyl)morpholine whereupon formation of the titanamine complex occurred.

Preparation of dihydropyridine compound

A solution of 4.10 grams (20 millimoles) of methyl 3-benzylaminocrotonate in 5 milliliters of dry benzene was added to the titanamine complex. After stirring for 5 minutes 1.20 grams (10 millimoles) of o-tolualdehyde was added. After about 6 hours of stirring at room temperatures, the reaction was poured into 100 milliliters of 1N hydrochloric acid and extracted with diethyl ether. The ether extract was washed successively with 1N hydrochloric acid, saturated sodium bicarbonate solution and brine, then dried over sodium sulfate. Removal of solvent at reduced pressure produced a yellow oil. Diethyl ether and hexane were added with stirring whereupon the dimethyl 1-benzyl-2,6-dimethyl-4-(2-methylphenyl)-1,4-dihydropyridine-3,5-dicarboxylate product formed as a white solid, 1.76 grams (43 percent). Additional product was obtained by column chromatography of the residue left after removal of the solvent from the mother liquor, 0.66 gram (16 percent). An analytical sample was prepared by recrystallization from CHCl$_3$/OEt$_2$, m.p.=144.5°–5.5° C. $^1$H NMR (CDCl$_3$, 360 MHz) δ 7.0–7.4 (m, 9H), 5.27 (s, 1H), 4.93 (s, 2H), 3.63 (s, 6H), 2.49 (s, 3H), 2.37 (s, 6H). Elemental analyses were as follows: Calc'd for C$_{24}$H$_{25}$NO$_4$: C, 74.05; H, 6.71; N, 3.45. Found: C, 74.31; H, 6.79; N, 3.39.

EXAMPLE II

Dimethyl 1-Benzyl-2,6-dimethyl-4-(2-methylphenyl)-1,4-dihydropyridine-3,5-dicarboxylate

Preparation of methyl 3-benzylaminocrotonate

Compound was prepared as described in Example I.

Preparation of the titanamine complex 0.55 milliliter (5 millimoles) of titanium tetrachloride was added to 20 milliliters of dried benzene under an atmosphere of argon to obtain a benzene solution of titanium tetrachloride. To this solution was added dropwise with rapid stirring. 1.07 grams (10 millimoles) of benzylamine whereupon a benzylamine titanium (titanamine) complex formed.

Preparation of the dihydropyridine compound

A solution of 4.10 grams (20 millimoles) of methyl 3-benzylaminocrotonate in 5 milliliters of dry benzene was added to the titanamine complex. Stirring was continued for 5 to 10 minutes. Then a solution of 1.20 grams (10 millimoles) of o-tolualdehyde in 5 milliliters of dry benzene was added with stirring. The mixture was stirred for three hours at ambient temperature. At the end of this time, it was poured into 200 milliliters of 1N hydrochloric acid and the resulting mixture thereafter extracted with diethyl ether. The ether solution was washed successively with 1N hydrochloric acid, saturated sodium bicarbonate solution and brine, then dried over sodium sulfate. The dried solution, after filtering, was subjected to reduced pressure to obtain a yellow oil as residue. NMR analysis of the residue indicated the oil to be 60 percent dimethyl 1-benzyl-2,6-dimethyl-4-(2-methylphenyl)-1,4-dihydropyridine-3,5-dicarboxylate. Diethyl ether was added to the oil whereupon a white solid formed which was determined by thin layer chromatographic analysis to be substantially completely the desired product.

EXAMPLE III

Dimethyl 1-(3-Butenyl)-2,6-dimethyl-4-phenyl-1,4-dihydropyridine-3,5-dicarboxylate

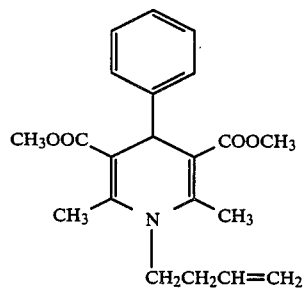

Preparation of methyl-3-(3-butenylamino)crotonate 2.15 milliliters (2.32 grams, 20.0 millimoles) of methyl acetoacetate was added with stirring to 1.42 grams (20.0 millimoles) of homoallylamine cooled in an ice bath and the stirring continued while the mixture was allowed to warm to room temperature and thereafter for three hours to obtain a methyl 2-(3-butenyl)aminocrotonate intermediate product and water by-product in the reaction mixture.

20 milliliters of diethyl ether was added to dissolve the intermediate ester product and the ether solution separated from the aqueous layer. The ether solution was washed with brine, then dried over sodium sulfate, the dried solution purified by passing through a silica gel pad, and the purified solution subjected to reduced pressure to remove the solvent and to recover 3.35 grams of methyl 3-(3-butenyl)aminocrotonate as an oil.

Preparation of titanamine complex and dihydropyridine compound

To a solution of 0.80 gram (4.2 millimoles) of titanium tetrachloride in 17 milliliters of benzene under an atmosphere of nitrogen, was added dropwise with rapid stirring, 0.72 gram (8.5 millimoles) of piperidine whereupon a green mixture was produced. To this mixture was added dropwise a freshly prepared solution of 2.88 grams (17 millimoles) of methyl 3-(3-butenyl)aminocrotonate in 4 milliliters of benzene. A reaction took place with the formation of a dark purple mixture. The mixture was stirred for an additional 5 minutes and then, to it was added dropwise a solution of 0.90 gram (8.5 millimoles) of benzaldehyde in 4 milliliters of benzene and stirring was continued for three hours at which time the reaction was quenched by adding 35 milliliters of 3N hydrochloric acid. The mixture was extracted with three 100 millilter portions of diethyl ether and the ether extract washed successively with 3N hydrochloric acid, saturated aqueous sodium bicarbonate and brine, and then dried over sodium sulfate. The solvent was vaporized from the dried solution under reduced pressure to obtain a yellow oil which when triturated with ether produced a white solid of dimethyl (1-(3-butenyl)-2,6-dimethyl-4-phenyl-1,4-dihydropyridine-3,5-dicarboxylate, m.p. 108°–110° C. and R$_f$0.4 on silica gel when eluted with 2:1 hexane/ether.

EXAMPLE IV

Dimethyl 2,6-Dimethyl-4-phenyl-1-[2-(3-thienyl)ethyl]-1,4-dihydropyridine-3,5-dicarboxylate

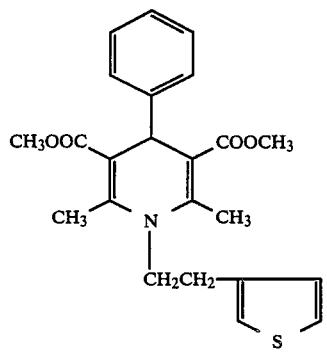

Preparation of methyl 3-(3-thienylethyl)aminocrotonate 3.8 grams (30 millimoles) of 3-(2-aminoethyl)thiophene was added dropwise with stirring at room temperature to 3.6 grams (31 millimoles) of methyl acetoacetate and the stirring was continued over the weekend at ambient temperature. Thereafter, the mixture was diluted with 250 milliliters of diethyl ether and the resulting ether solution washed with 50 milliliters of brine and then dried over sodium sulfate. The ether solvent was then vaporized from the dried and filtered solution to obtain 6.59 grams of a methyl 3-[(3-thienyl)ethyl]aminocrotonate intermediate as a slightly yellowish oil.

Preparation of titanamine complex and dihydropyridine compound

To 45 milliliters of benzene under a nitrogen atmosphere was added first, 0.84 milliliter (7.5 millimoles) of titanium tetrachloride and then dropwise 1.9 grams (15 millimoles) of 3-(2-aminoethyl)thiophene. The mixture became slightly warm and an orange precipitate appeared. To this mixture was added dropwise, 6.59 grams (29.2 millimoles) of freshly prepared methyl 3-(3-thienylethyl)aminocrotonate and 1.59 grams (15 millimoles) of benzaldehyde in 25 milliliters of benzene whereupon a reaction occurred with the formation of a dimethyl 2,6-dimethyl-4-phenyl-1-[2-(3-thienyl)ethyl]-1,4-dihydropyridine-3,5-dicarboxylate compound as a yellow suspension. Stirring of the reaction mixture was continued at ambient temperature overnight to continue the formation of the intermediate product.

Thereafter, the reaction mixture was poured into a solvent mixture of 150 milliliters of 2N hydrochloric acid and 350 milliliters of methylene chloride, and thoroughly contacted by shaking. The aqueous and organic phases then were separated. The aqueous solution was extracted with two 100 milliliter portions of methylene chloride, the methylene chloride solutions were combined, and the combined methylene chloride solution was washed with brine and dried. The dried solution was filtered through a silica gel pad and the solvent vaporized to recover a yellow oil. 40 milliliters of hexane containing 2 milliliters of ether was added to the yellow oil and stirred at room temperature whereupon a white solid separated. A portion of the solid was recrystallized from hexane to obtain purified dimethyl 2,,6-dimethyl-4-phenyl-1-[2-(3-thienyl)ethyl]-1,4-dihydropyridine-3,5-dicarboxylate product, m.p. 127.5°–128.5° C.

EXAMPLE V

Diethyl 1-(3-Butenyl)-2,6-dimethyl-4-(3-trifluoromethylphenyl)-1,4-dihydropyridine 3,5-dicarboxylate

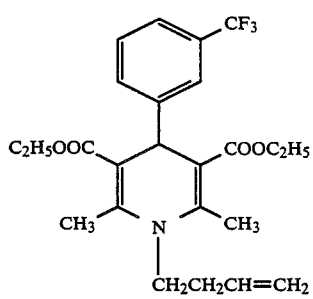

In a manner similar to that described in Example 2, 2.6 grams (20 millimoles) of ethyl acetoacetate is added with stirring to 1.42 moles (20 millimoles) of homoallylamine cooled in an ice bath and the stirring continued with gradual warming to ambient temperature to otain an ethyl 3-(3-butenyl)aminocrotonate ccompound in the reaction mixture. The crotonate compound is recovered by dissolving in ether, washing and drying the ethereal solution, then vaporizing the solvent under reduced pressure.

A solution of 1.83 grams (10 millimoles) of the crotonate compound in 5 milliliters of benzene is added dropwise with stirring under an atmosphere of nitrogen to a titanamine complex mixture prepared from 0.37 gram (4.3 millimoles) of piperidine and 0.4 gram (2.1 millimoles) of titanium tetrachloride in 10 milliliters of benzene and the stirring continued for five minutes. A solution of 0.75 gram (4.3 millimoles) of 3-trifluoromethylbenzaldehyde in 5 milliliters of benzene then is added and the stirring continued for several hours with the formation of a diethyl 1-(3-butenyl)-2,6-dimethyl-4-(3-trifluoromethylphenyl)-1,4-dihydropyridine-3,5-dicarboxylate product. Thereafter, the reaction is quenched with dilute hydrochloric acid and the product recovered as described in Example I.

EXAMPLE VI

Diethyl 2,6-Diethyl-4-(3-methoxyphenyl)-1-[2-(3,4-methylenedioxypheny)ethyl]-1,4-dihydropyridine-3,5-dicarboxylate

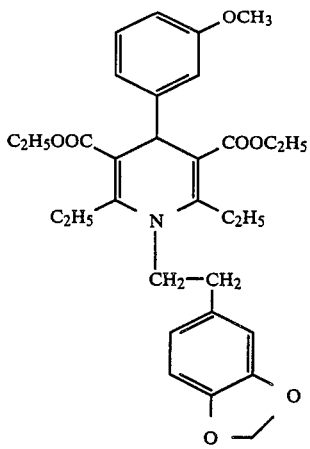

In a manner similar to that described in Example IV, 5.0 grams (30 millimoles) of 4-(3,4-methylenedioxyphenethylamine is added dropwise with stirring at ambient temperature to 4.5 grams (31 millimoles) of ethyl propionylacetate and the stirring continued for about 12 hours at ambient temperature. Thereafter, the mixture is diluted with 250 milliliters of diethyl ether and the resulting ether solution washed with 50 milliliters of brine and then dried over sodium sulfate. The ether is vaporized off of the dried and filtered solution to obtain ethyl 3-[2-(3,4-methylenedioxyphenyl)ethyl]amino-2-pentenoate.

To 45 milliliters of benzene is added 0.84 milliliter (7.5 millimoles) of titanium tetrachloride and 2.5 grams (15 millimoles) of 3,4-methylenedioxyphenethylamine. To the mixture then is added a solution of 8.7 grams (30 millimoles) of ethyl 3-[2-(3,4-methylenedioxyphenyl)ethyl]amino-2-pentenoate and 2.0 grams (15 millimoles) of 3-methoxybenzaldehyde in 25 milliliters of benzene and the resulting mixture stirred at ambient temperature overnight to obtain diethyl 2,6-diethyl-4-(3-methoxyphenyl)-1-[2-(3,4-methylenedioxyphenyl)ethyl]-1,4-dihydropyridine-3,5-dicarboxylate product in the reaction mixture. The product then is recovered as described in Example IV.

EXAMPLE VII

Di-(n-hexyl) 1-(3-Butenyl)-2,6-dimethyl-4-(3-nitrophenyl)-1,4-dihydropyridine-3,5-dicarboxylate

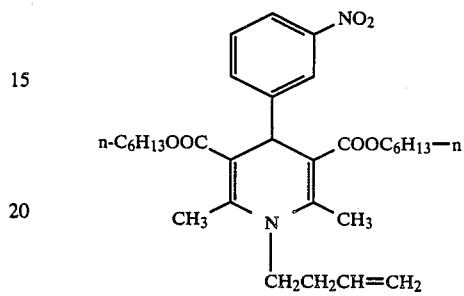

In a manner similar to that described in the preceding example, n-hexyl acetoacetate is added dropwise to a cooled solution of homoallylamine, the mixture stirred first while being cooled and then while being allowed to warm to ambient temperature to obtain therein n-hexyl 3-(3-butenyl)aminocrotonate. The ester is recovered in a manner similar to that previously described and is then dissolved in benzene and the benzene solution of the ester added dropwise with stirring under an atmosphere of nitrogen to a solution of titanamine prepared by mixing together titanium tetrachloride and piperidine. This is followed by addition of a benzene solution of 3-nitrobenzaldehyde to obtain therein a di-(n-hexyl)1-(3-butenyl)-2,6-dimethyl-4-(3-nitrophenyl)-1,4-dihydropyridine-3,5-dicarboxylate product. The product may then be recovered in a conventional manner.

EXAMPLES VIII–XXVIII

In operations carried out in a manner similar to that described in Examples I–VII, the following compounds may be prepared:

TABLE

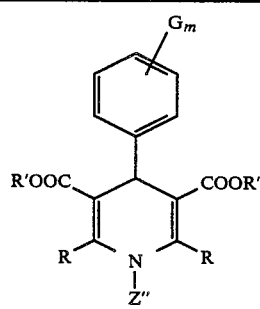

| Example | G | m | R | R' | Z'' |
|---|---|---|---|---|---|
| VIII | 2,3-Cl | 2 | —CH$_3$ | —C$_2$H$_5$ | —CH$_2$CH$_2$— 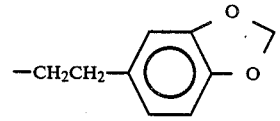 |

TABLE-continued

[Structure: 1,4-dihydropyridine with 4-aryl group bearing $G_m$ substituents, 3,5-dicarboxylate (R'OOC, COOR'), 2,6-disubstituted with R, and N-Z'' on ring nitrogen]

| Example | G | m | R | R' | Z'' |
|---------|---|---|---|----|----|
| IX | 2-$CH_3$ | 1 | —$CH_3$ | —$CH_3$ | —$CH_2CH_2$—N(morpholine) |
| X | 2,3-$OCH_2O$— | 2 | —$CH_3$ | —$C_4H_9n$ | —$CH_2$-cyclohexyl |
| XI | 2,3,4,5,6-F | 5 | —$CH_3$ | —$CH_2$—$C_6H_5$ | —$CH_2CH_2COCH_3$ |
| XII | 2-Br, 4,5-$OCH_3$ | 3 | —$CH_3$ | —$C_2H_5$ | —$CH(CH_3)_2$ |
| XIII | 2-$CF_3$ | 1 | —$nC_3H_7$ | —$C_2H_5$ | —$CH_2CH_2OCC_6H_5$ (with C=O) |
| XIV | 4-n-$C_5H_{11}$ | 1 | —$C_2H_5$ | —$C_2H_5$ | —$CH_2CH_2N(CH_3)C_6H_5$ |
| XV | 4-$CH_2CH=CH_2$, 3-$OCH_3$ | 2 | —$CH_2CH_2CH_2CH(CH_3)_2$ | —$C_2H_5$ | —$CH_2CH_2N(CH_3)C_4H_9$ |
| XVI | 4-$SC_3H_7$ | 1 | —n-$C_5H_{11}$ | —$C_2H_5$ | —$CH_2$-(2-thienyl) |
| XVII | 4-$N(CH_3)_2$ | 1 | —$CH_2CH_2OCH_3$ | —$CH_3$ | —$CH_2CH_2$-(4-pyridyl) |
| XVIII | 2-$OC_3H_7$ | 1 | —$CH_3$ | —$CH_2CH_2OCH_3$ | —$CH_2CH_2$-(2,3-dimethoxyphenyl) |
| XIX | 2-Cl, 5-$NO_2$ | 2 | —$CH_3$ | —$CH_2CH_2OCH_3$ | —$CH_2CH_2SC_6H_5$ |
| XX | (benzofurazan-4-yl) | — | —$CH_3$ | —$CH_2C_6H_5$ | cyclohexyl |
| XXI | 3-CN | 1 | —$CH_3$ | —$CH_2CH=CH_2$ | —n-$C_6H_{13}$ |
| XXII | 2-$OCF_2H$ | 1 | —$CH_3$ | —$CH(CH_3)_2$ | —$CH_2CH_2$-(1-methylpyrrol-2-yl) |

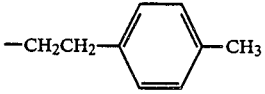

| Example | G | m | R | R' | Z'' |
|---|---|---|---|---|---|
| XXIII | 3-CH₂OCH₃ | 1 | —CH₃ | —CH(CH₃)C₆H₅ | —CH₂CO₂CH₃ |
| XXIV | 2-CH=CH₂ | 1 | —CH₃ | —CH₃ | —CH₂CH₂-C₆H₄-CH₃ |
| XXV | 2-SC(CH₃)₃ | 1 | —CH₃ | —CH₂CH₂OCH₃ | —CH₂CH₂-(2,3-Cl₂C₆H₃) |
| XXVI | 4-CH(CH₃)₂ | 1 | —CH₃ | —CH₃ | —CH₂CH₂CH=CH₂ |
| XXVII | 3,4,5-OCH₃ | 3 | —CH₃ | —CH(CH₃)₂ | —CH₂CH₂-(2-naphthyl) |
| XXVIII | 2-SCH₃, 5-NO₂ | 2 | —CH₃ | —C₂H₅ | —CH₂C≡CH |

EXAMPLE XXIX

Diethyl 2,6-Dimethyl-4-(2-methylphenyl)-1,4-dihydropyridine-3,5-dicarboxylate

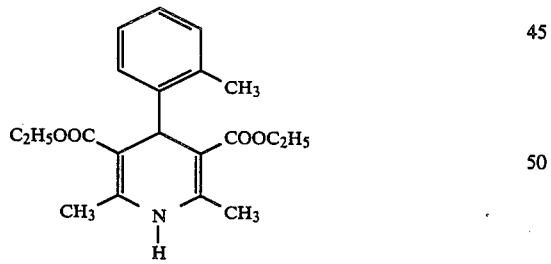

Under an atmosphere of argon, 0.89 milliliter (5 millimoles) of 4-(trimethylsilyl)morpholine was added with stirring to a solution of 0.55 milliliter (1.73 grams, 5 millimoles) of titanium tetrachloride in 20 milliliters of dry benzene and stirring was continued at ambient temperature for ten minutes. Then, 2.58 grams (20 millimoles) of ethyl aminocrotonate was added, followed by 1.20 grams (10 millimoles) of o-tolualdehyde. The stirring was continued for 1.5 hours. Thereafter, the reaction mixture was poured into 200 milliliters of 1N hydrochloric acid and extracted with diethyl ether. The extract was washed successively with 1N-hydrochloric acid, saturated sodium bicarbonate solution and brine. The ether extract was dried and stripped of the solvent to obtain a yellow oil as residue. The oil was purified by flash chromatography on silica employing 2:1 hexane/diethyl ether to obtain 1.39 grams of the desired diethyl 2,6-dimethyl-4-(2-methylphenyl)-1,4-dihydropyridine-3,5-dicarboxylate product, m.p. 128°-9.5° C.; ¹H NMR (CDCl₃, 360 MHz) 7.32 (d, 1H), 7.0–7.1 (m, 3H), 5.57 (broad 5, 1H), 5.16 (s, 1H), 4.08 (qq, 4H), 2.56 (s, 3H), 2.31 (s, 6H), 1.21 (t, 7.1 Hz, 6H). Elemental analyses were as follows: Anal. Calcd. for C₂₀H₂₅NO₄: C, 69.95; H, 7.34, N, 4.08. Found: C, 69.88; H, 71.60; N, 4.04.

EXAMPLE XXX

Dimethyl 2,6-Dimethyl-4-phenyl-1-(2-methylphenyl)-1,4-dihydropyridine-3,5-dicarboxylate

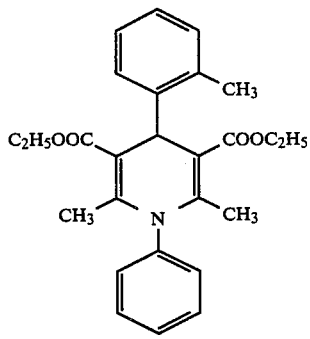

In a manner similar to that previously described, 96.4 grams (0.9 mole) of o-toluidine is added dropwise to a solution of 116 grams (1 mole) of methyl acetoacetate and the reaction mixture allowed to stand overnight to obtain methyl 3-(2-methylphenyl)aminocrotonate.

To a solution of 0.55 milliliter of titanium tetrachloride in 20 milliliters of chloroform is added under nitrogen, 1.07 grams (10 millimoles) of o-toluidine to obtain a titanamine complex.

A solution of 4.1 grams (20 millimoles) of methyl 3-(2-methylphenyl)aminocrotonate in 5 milliliters of dry benzene is added to the titanamine complex followed by 1.1 grams (10 millimoles) of benzaldehyde and the mixture stirred at ambient temperature for several hours to obtain the desired dimethyl 2,6-dimethyl-4-phenyl-1-(2-methylphenyl)-1,4-dihydropyridine-3,5-dicarboxylate which may be recovered in a manner similar to that previously described.

Preparation of Starting Material

The acylacetic ester starting materials may be prepared by standard methods such as by reacting together substantially equimolar proportions of the appropriate acyl halide and an O-silyl ketone acetal in tetrahydrofuran and in the presence of triethylamine for time sufficient to complete the reaction and thereafter acidifying to obtain the acylacetic acid ester as more fully described by Rathke and Sullivan, Tet. Lett., 1297–1300 (1973).

Many aromatic aldehydes are available commercially. They also may be prepared by reacting aryllithium with N-formylpiperidine in an inert solvent such as ether or tetrahydrofuran at about 0° C. as more fully described in a paper by Olah et al, Angew. Chem. Int. Ed. Eng., 20 878–9 (1981).

What is claimed is:

1. A process for preparing a dihydropyridine compound represented by the formula:

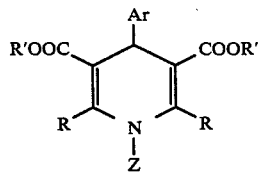

which comprises reacting under inert atmosphere, an aminoalkenoate compound

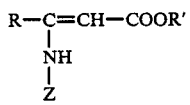

and an aryl aldehyde compound

Ar—CHO in the presence of a titanamine reagent for time sufficient to complete the reaction, wherein Ar is a substituted or unsubstituted carbocyclic aryl or substituted or unsubstituted heterocyclic aryl, R is alkyl or substituted alkyl; R' is alkyl, alkenyl, cycloalkyl, substituted alkyl or benzyl, and Z is hydrogen, alkyl, alkenyl, alkynyl, cycloalkyl, phenyl, tolyl, substituted alkyl, substituted alkenyl and substituted alkynyl.

2. A process according to claim 1 wherein
Ar is a carbocyclic aryl radical, a heterocyclic aryl radical, a substituted carbocyclic aryl radical with up to three substituents, a substituted heterocyclic aryl radical with up to two substituents, perfluorophenyl or benzoxadiazolyl; wherein the carbocyclic aryl radical is of 6 or 10 atoms, the heterocyclic radical is of 5 or 6 atoms of which one or two is a heteroatom selected from O, S or N, and in the substituted radicals, the substituent is selected from $C_1$–$C_8$ alkyl, $C_2$–$C_8$ alkenyl, $C_1$–$C_8$ alkoxy, $C_2$–$C_8$ alkoxyalkyl, $C_1$–$C_2$ alkylenedioxy, $C_2$–$C_8$ dialkylamino, $C_1$–$C_8$ alkylthio, chloro, fluoro, bromo, iodo, cyano, nitro trifluoromethyl, and mono- and polyhalomethoxy wherein the halo may be fluor, chloro or bromo;

R is alkyl or substituted alkyl; wherein when alkyl, it is of 1 to 8 carbon atoms and when substituted alkyl, the alkyl portion is of 1 to 3 carbon atoms and the substituent is selected from $C_1$–$C_4$ alkoxy and $C_1$–$C_4$ mono- or polyhaloalkyloxy wherein the halo may be fluoro, chloro or bromo;

R' is alkyl, alkenyl, cycloalkyl, substituted alkyl or benzyl; wherein alkyl is of 1 to 8 carbon atoms, alkenyl is of 2 to 8 carbon atoms, cycloalkyl is of 3 to 6 carbon atoms, and substituted alkyl is of 2 to 4 carbon atoms in the alkyl portion and is substituted at the 2 or higher position with a substituent selected from $C_1$–$C_8$ alkoxy, fluoro, chloro, bromo, $C_2$–$C_8$ dialkylamino, phenyl, and a heterocyclic aryl radical of 5 or 6 atoms containing up to 3 hetero atoms selected from O, S and N;

Z is hydrogen, alkyl, alkenyl, alkynyl, phenyl, tolyl, cycloalkyl, phenyl substituted alkyl, substituted alkenyl and substituted alkynyl; wherein alkyl is a radical of from 1 to 10 carbon atoms; alkenyl is a radical of from 3 to 10 carbon atoms with the olefinic unsaturation occurring at the 2 or higher position; alkynyl is a radical of from 3 to 10 carbon atoms with the acetylenic unsaturation occurring at the 2 or higher position; cycloalkyl is a radical of from 3 to 6 carbon atoms; substituted alkyl is a radical of up to 10 carbon atoms in the alkyl portion and wherein the substituent may be selected from Ar as above-defined, $C_3$–$C_6$ cycloalkyl or $C_2$–$C_8$ carboalkoxy, or when the alkyl group is at least of 2 carbon atoms, it may be substituted at the 2 or higher position with a substituent selected from $C_1$–$C_8$ alkoxy, $C_1$–$C_8$ alkylthio, fluoro, chloro, bromo, $C_2$-$C_8$ dialkylamino, phenoxy, phenylthio, morpholino, piperidino, pyrrolidino, piperazino and $C_2$-$C_8$ acyloxy, substituted alkenyl wherein the substituent is selected from Ar as above defined, $C_3$-$C_6$ alkyl, and $C_2$-$C_8$ carboalkoxy; and substituted alkynyl wherein the substituent is selected from Ar as above defined, $C_3$-$C_6$ cycloalkyl and $C_2$-$C_8$ carboalkoxy.

3. A process according to claim 1 wherein the aminoalkenoate compound and the aldehyde compound are added simultaneously in a solution containing both to the titanamine reagent mixture.

4. A process according to claim 1 wherein the aminoalkenoate compound and the aldehyde compound are added sequentially.

5. A process according to claim 1 wherein the titanamine reagent is that formed from titanium tetrachloride and a secondary amine.

6. A process according to claim 5 wherein the titanamine reagent employed has a ratio of amine base to titanium tetrachloride of about 2.5:1 to 1.8:1.

7. A process according to claim 1 wherein the titanamine reagent is that formed from titanium tetrachloride and a tertiary trimethylsilylamine.

8. A process according to claim 7 wherein the titanamine reagent employed has a ratio of amine base to titanium tetrachloride of 1.2:1 to 0.8:1.

9. A process according to claim 1 wherein the titanamine reagent is that formed from titanium tetrachloride and an amine base of the same kind as that which is incorporated in the final dihydropyridine structure.

10. A process according to claim 9 wherein the titanamine reagent employed has a ratio of amine base to titanium tetrachloride of about 2.5:1 to 1.8:1.

11. A process for preparing a dihydropyridine compound represented by the formula:

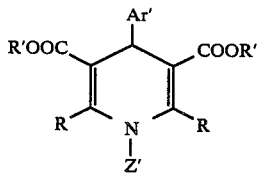

wherein:
Ar' is phenyl; substituted phenyl with up to 3 substituents selected from $C_1$-$C_8$ alkyl, $C_2$-$C_8$ alkenyl, $C_1$-$C_8$ alkoxy, $C_2$-$C_8$ alkoxyalkyl, $C_1$-$C_2$ alkylenedioxy, $C_2$-$C_8$ dialkylamino, $C_1$-$C_8$ alkylthio, fluoro, chloro, bromo, iodo, trifluoromethyl, cyano, nitro, and mono- and polyhalomethoxy wherein each halo is selected from fluoro, chloro and bromo; perfluorophenyl; or benzoxadiazolyl;

R is $C_1$-$C_8$ alkyl; or $C_1$-$C_3$ substituted alkyl with the substituent selected from $C_1$-$C_4$ alkoxy and $C_1$-$C_4$ mono- or polyhalo alkoxy wherein the halo is selected from fluoro, chloro and bromo;

R' is $C_1$-$C_8$ alkyl; $C_2$-$C_8$ alkenyl; $C_3$-$C_6$ cycloalkyl; $C_2$-$C_4$ substituted alkyl wherein the substituent is at a 2 or higher position and is selected from $C_1$-$C_8$ alkoxy, fluoro, chloro, bromo, $C_2$-$C_8$ dialkylamino, phenyl, and a heterocyclic aryl radical of 5 or 6 atoms containing up to 3 hetero atoms selected from O, S and N; or benzyl;

Z' is $C_1$-$C_{10}$ alkyl; $C_3$-$C_{10}$ alkenyl wherein the olefinic unsaturation occurs at the 2 or higher position; $C_3$-$C_{10}$ alkynyl wherein the acetylenic unsaturation occurs at the 2 or higher position; $C_3$-$C_6$ cycloalkyl; $C_1$-$C_{10}$ substituted alkyl with the substituent selected from Ar' as above defined, $C_3$-$C_6$ cycloalkyl, $C_2$-$C_8$ carboalkoxy, naphthyl, and a heterocyclic radical of 5 or 6 carbon atoms of which one or two is a hetero atom selected from O, S and N, and which heterocyclic radical may be substituted with $C_1$-$C_4$ alkyl; $C_2$-$C_{10}$ substituted alkyl with the substituent at the 2 or higher position and the substituent is selected from $C_1$-$C_8$ alkoxy, $C_1$-$C_8$ alkylthio, fluoro, chloro, bromo, iodo, alkylthio, fluoro, chloro, bromo, iodo, $C_2$-$C_8$ dialkylamino, phenoxy, phenylthio, morpholino, piperidino, pyrrolidino, piperazino and $C_2$-$C_8$ acyloxy; $C_3$-$C_{10}$ alkenyl substituted with a substituent selected from Ar' as above defined, $C_3$-$C_6$ cycloalkyl, and $C_2$-$C_8$ carboalkoxy; $C_3$-$C_{10}$ alkynyl substituted with a substituent selected from Ar' as above defined, $C_3$-$C_6$ cycloalkyl, and $C_2$-$C_8$ carboalkoxy;

which comprises
(1) intimately contacting an acylacetate ester compound

with an amine compound

to form an aminoalkenoate compound

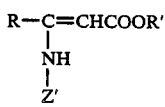

(2) intimately contacting an organic amine under an inert atmosphere with titanium tetrachloride in an inert solvent to form a titanamine reagent (3) intimately contacting under an inert atmosphere the titanamine reagent, the aminoalkenoate compound prepared in accordance with Step (1) and an aromatic aldehyde compound,

for time sufficient to complete the reaction.

12. A process for preparing a dihydropyridine compound represented by the formula

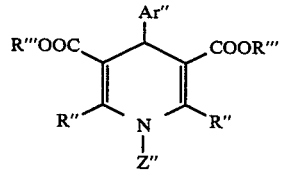

wherein:
Ar" is perfluorophenyl; benzoxadiazolyl; or a radical represented by

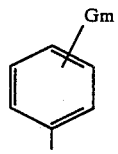

wherein G is $C_1$-$C_8$ alkyl; $C_2$-$C_8$ alkenyl; $C_1$-$C_8$ alkoxy, $C_2$-$C_8$ alkoxyalkyl, $C_1$-$C_2$ alkylenedioxy, $C_2$-$C_8$ dialkylamino, $C_1$-$C_8$ alkylthio, fluoro, chloro, bromo, iodo, trifluoromethyl, cyano, nitro, and mono- and polyhalomethoxy wherein halo is selected from fluoro, chloro and bromo; and m is 0-3;

R'' is $C_1$-$C_8$ alkyl; or $C_2$-$C_8$ alkoxyalkyl;

R''' is $C_1$-$C_8$ alkyl; $C_2$-$C_8$ alkenyl; $C_2$-$C_4$ substituted alkyl wherein the substituent is at the 2 or higher position and is selected from $C_1$-$C_8$ alkoxy, $C_2$-$C_8$ dialkylamino, phenyl and pyridyl; or benzyl;

Z'' is $C_1$-$C_{10}$ alkyl; $C_3$-$C_{10}$ alkenyl wherein the olefinic unsaturation occurs at the 2 or higher position; $C_3$-$C_{10}$ alkynyl wherein the acetylenic unsaturation occurs at the 2 or higher position; $C_3$-$C_6$ cycloalkyl; $C_1$-$C_{10}$ substituted alkyl with the substituent selected from Ar'' as above defined, $C_3$-$C_6$ cycloalkyl, and $C_2$-$C_8$ carboalkoxy, naphthyl, and a heterocyclic radical of 5 or 6 carbon atoms of which one or two is a hetero atom selected from O, S, and N, and which heterocyclic radical may be substituted with $C_1$-$C_4$ alkyl; $C_2$-$C_{10}$ substituted alkyl with the substituent at the 2 or higher position and the substituent selected from $C_1$-$C_8$ alkoxy, $C_1$-$C_8$ alkylthio, fluoro, chloro, bromo, iodo, $C_2$-$C_8$ dialkylamino, N-alkylanilino, phenoxy, phenylthio, morpholino, piperidino, pyrrolidino, piperazino and $C_2$-$C_8$ acyloxy; $C_3$-$C_{10}$ alkenyl substituted with Ar'' as above defined, $C_3$-$C_6$ cycloalkyl or $C_2$-$C_8$ carboalkoxy; $C_3$-$C_{10}$ alkynyl substituted with a substituent selected from Ar'' as above defined, $C_3$-$C_6$ cycloalkyl, and $C_2$-$C_8$ carboalkoxy;

which comprises (1) intimately contacting an acylacetate ester compound

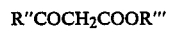

R''COCH$_2$COOR''' and an amine compound

H$_2$N—Z'' by adding dropwise one component to the other and stirring together for a time sufficient to complete the reaction with the formation of an aminoalkenoate compound

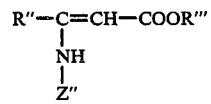

(2) in a separate operation, adding an organic amine dropwise in an inert atmosphere, to a stirred solution of titanium tetrachloride in an inert hydrocarbon solvent to form a titanamine reagent mixture and (3) adding dropwise to the titanamine reagent mixture while in an inert atmosphere the aminoalkenoate compound prepared in accordance with Step (1) and an aldehyde compound

Ar''CHO in an organic solvent and stirring the resulting mixture together for time sufficient to complete the reaction.

13. A process for preparing a dihydropyridine compound represented by the formula:

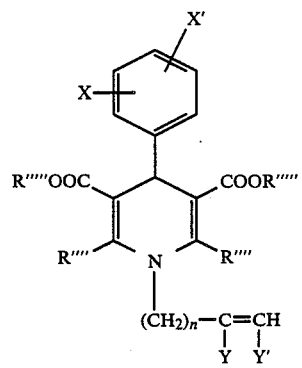

wherein:

X and X' are independently hydrogen, halogen, lower alkyl, lower alkoxy, nitro or trifluoromethyl;

R'''' is lower alkyl;

R''''' is lower alkyl;

Y and Y' independently are hydrogen or lower alkyl, or together may be CH=CH—S—, —CH=CH—O—, —CH=CH—NH— or —CH=CH—NAlk—;

n is 2 or 3;

which comprises:

(1) reacting an acylacetate ester compound represented by the formula:

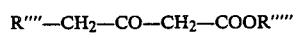

R''''—CH$_2$—CO—CH$_2$—COOR''''' with an amine compound represented by the formula:

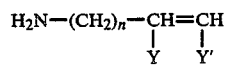

to obtain an aminoalkenoate compound represented by the formula:

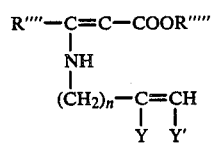

and (2) reacting the aminoalkenoate compound with an aldehyde compound represented by the formula:

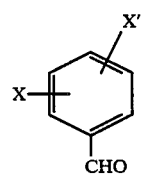

in the presence of a titanamine catalyst.

14. A process for preparing a dihydropyridine compound represented by the formula:

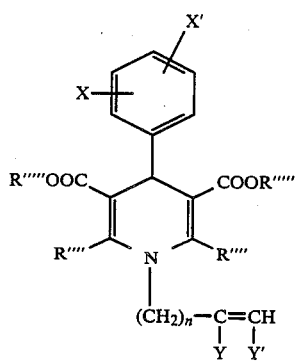

wherein:

X and X' are independently hydrogen, halogen, lower alkyl, lower alkoxy, nitro or trifluoromethyl;

R''''' is lower alkyl;

R'''' is lower alkyl;

Y and Y' are independently hydrogen or lower alkyl, or together may be —(CH$_2$)$_{3-4}$—, —CH=CH—CH$_2$—, CH=CH—S—, —CH=CH—O—, or —CH=CH—NAlk—;

n is 2 or 3;

which comprises:

(1) intimately contacting an acylacetate ester compound

R''''—CO—CH$_2$—COOR''''' and an amine compound

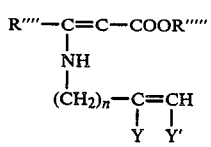

by adding dropwise one component to the other and stirring together for time sufficient to complete the reaction with the formation of an aminoalkenoate compound

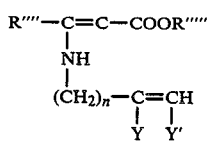

(2) adding in an inert atmosphere an organic amine, to a stirred solution of titanium tetrachloride in an inert hydrocarbon solvent to form a titanamine reagent, (3) adding dropwise in an inert atmosphere to the titanamine reagent, a solution of the aminoalkenoate compound and an aldehyde compound of the formula

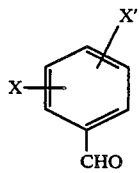

at ambient temperature and stirring the resulting mixture for time sufficient to complete the reaction.

* * * * *